US012670989B1

(12) United States Patent
Blackstone

(10) Patent No.: US 12,670,989 B1
(45) Date of Patent: Jun. 30, 2026

(54) SYSTEMS AND METHODS FOR AUTOMATED SPEECH-TO-TRANSACTION IN HEALTHCARE OPERATIONS

(71) Applicant: Michael Blackstone, Birmingham, AL (US)

(72) Inventor: Michael Blackstone, Birmingham, AL (US)

( * ) Notice: Subject to any disclaimer, the term of this patent is extended or adjusted under 35 U.S.C. 154(b) by 0 days.

(21) Appl. No.: 19/231,796

(22) Filed: Jun. 9, 2025

(51) Int. Cl.
| | |
|---|---|
| *G16H 40/20* | (2018.01) |
| *G06F 40/30* | (2020.01) |
| *G06Q 40/08* | (2012.01) |
| *G06Q 50/22* | (2024.01) |
| *G16H 10/60* | (2018.01) |
| *G16H 80/00* | (2018.01) |

(52) U.S. Cl.
CPC ............ *G16H 40/20* (2018.01); *G06F 40/30* (2020.01); *G06Q 40/08* (2013.01); *G06Q 50/22* (2013.01); *G16H 10/60* (2018.01); *G16H 80/00* (2018.01)

(58) Field of Classification Search
CPC ........ G16H 40/20; G16H 10/60; G16H 80/00; G06F 40/30; G06Q 40/08; G06Q 50/22
USPC ........................................................ 705/2–3
See application file for complete search history.

(56) References Cited

U.S. PATENT DOCUMENTS

| | | | | |
|---|---|---|---|---|
| 2024/0096455 A1* | 3/2024 | Holes | .................... | G16H 10/20 |
| 2025/0131997 A1* | 4/2025 | Forester | ................ | G16H 10/20 |
| 2025/0209402 A1* | 6/2025 | Gholap | .................. | G16H 40/20 |
| 2025/0298971 A1* | 9/2025 | Du | .......................... | G06F 40/56 |

OTHER PUBLICATIONS

Aramaki et al. "Natural Language Processing: from Bedside to Everywhere." Yearbook of medical informatics vol. 31,1 (2022): 243-253. doi:10.1055/s-0042-1742510 (Year: 2022).*

* cited by examiner

*Primary Examiner* — Joy Chng
(74) *Attorney, Agent, or Firm* — The Rapacke Law Group, P.A.; Andrew S. Rapacke; Kenneth F. Brooks

(57) ABSTRACT

A computer-implemented system and method enable real-time healthcare transaction processing based on ambient audio captured during physician-patient conversations. The system includes one or more microphones to receive spoken dialogue and a speech recognition engine to transcribe the audio into text. A natural language processing module analyzes the text to identify clinical intents corresponding to healthcare transactions. The identified intent is standardized into a structured query format and transmitted to an external system via a communications interface. In response, the system receives external data such as insurance coverage status, cost estimates, or authorization requirements. A user interface displays the external response in real time during the clinical encounter, allowing the physician or patient to make informed decisions. Additional modules may include context monitoring logic to suppress non-actionable utterances and a secure storage engine to log queries and responses. The system automates insurance verification and authorization workflows without requiring manual data entry.

19 Claims, 7 Drawing Sheets

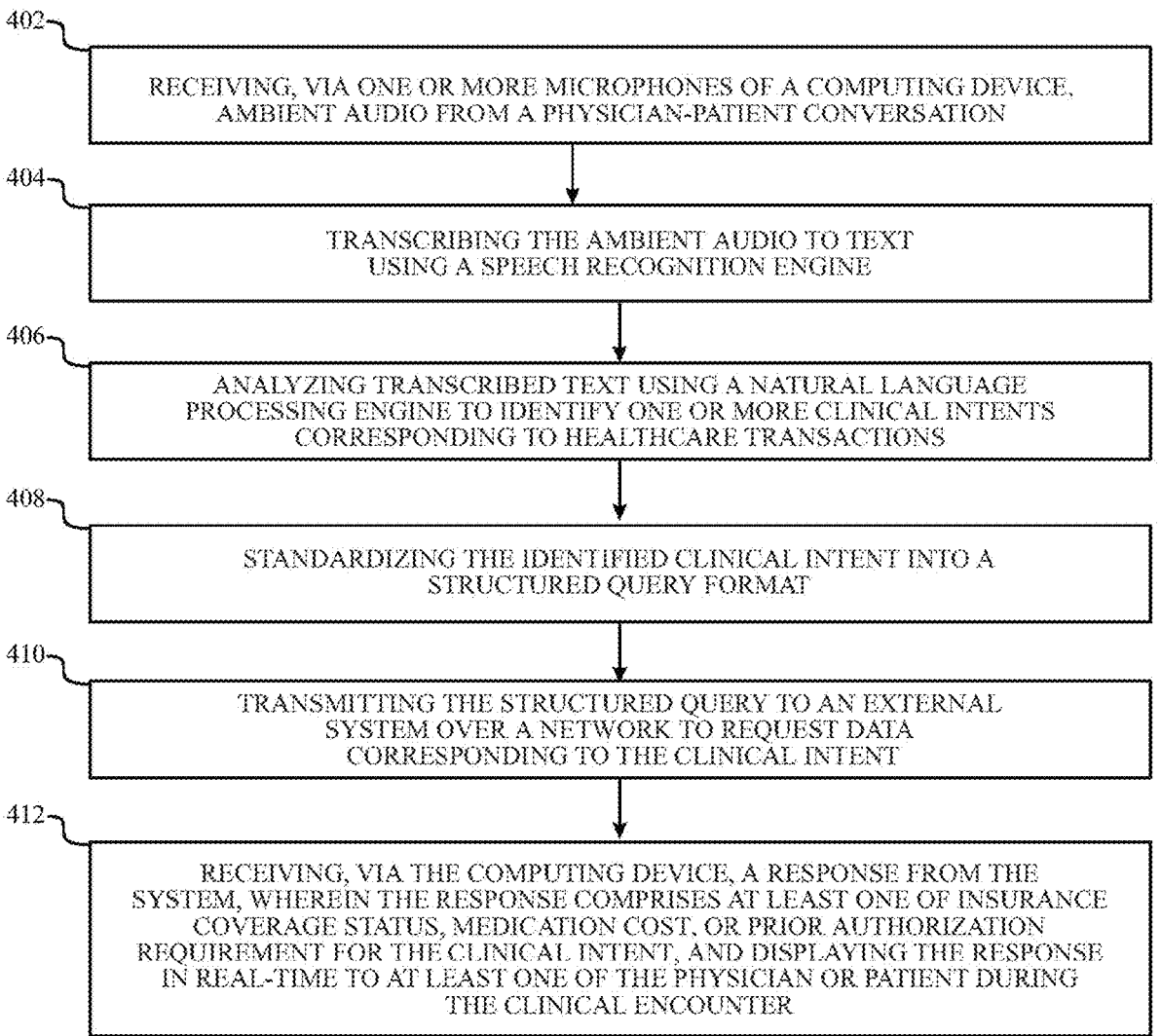

402 — RECEIVING, VIA ONE OR MORE MICROPHONES OF A COMPUTING DEVICE, AMBIENT AUDIO FROM A PHYSICIAN-PATIENT CONVERSATION

404 — TRANSCRIBING THE AMBIENT AUDIO TO TEXT USING A SPEECH RECOGNITION ENGINE

406 — ANALYZING TRANSCRIBED TEXT USING A NATURAL LANGUAGE PROCESSING ENGINE TO IDENTIFY ONE OR MORE CLINICAL INTENTS CORRESPONDING TO HEALTHCARE TRANSACTIONS

408 — STANDARDIZING THE IDENTIFIED CLINICAL INTENT INTO A STRUCTURED QUERY FORMAT

410 — TRANSMITTING THE STRUCTURED QUERY TO AN EXTERNAL SYSTEM OVER A NETWORK TO REQUEST DATA CORRESPONDING TO THE CLINICAL INTENT

412 — RECEIVING, VIA THE COMPUTING DEVICE, A RESPONSE FROM THE SYSTEM, WHEREIN THE RESPONSE COMPRISES AT LEAST ONE OF INSURANCE COVERAGE STATUS, MEDICATION COST, OR PRIOR AUTHORIZATION REQUIREMENT FOR THE CLINICAL INTENT, AND DISPLAYING THE RESPONSE IN REAL-TIME TO AT LEAST ONE OF THE PHYSICIAN OR PATIENT DURING THE CLINICAL ENCOUNTER

*FIG. 4*

SYSTEMS AND METHODS FOR AUTOMATED SPEECH-TO-TRANSACTION IN HEALTHCARE OPERATIONS

TECHNICAL FIELD

The embodiments generally relate to systems and methods for coordinated healthcare management through real-time speech-to-transaction processing.

BACKGROUND

Speech recognition technology has been integrated into healthcare settings to support clinical documentation and improve the efficiency of medical recordkeeping. Conventional systems typically capture audio during patient encounters, convert spoken language into text using automated speech recognition engines, and organize the transcribed text into structured notes or summaries. These systems often work in conjunction with electronic health records (EHR) to streamline the documentation process and reduce the manual workload for healthcare professionals.

Natural language processing has further advanced the capabilities of clinical software tools by enabling systems to interpret context and categorize sections of transcribed speech. These tools are designed to assist in organizing patient histories, diagnoses, and treatment plans. In some implementations, voice assistants and conversational agents allow users to interact with clinical applications through spoken commands, offering functionalities such as note-taking, appointment scheduling, and general inquiries about a patient's medical data. These systems typically rely on keyword detection and structured command formats to trigger specific responses or actions within a software interface.

While these conventional systems provide efficiencies in documentation and data entry, they generally operate within closed systems that focus on internal data management. Many of these tools are optimized for generating accurate medical notes or populating patient charts but are not designed to query, submit transactions, nor communicate in real-time with systems external to the healthcare provider ("external systems") (i.e. insurance systems, drug assistance programs, and the system, methods, and software mediums covered by this patent) based on conversation alone. As a result, any follow-up actions, particularly those that involve external databases, such as verifying insurance coverage or submitting prior authorizations, usually require manual input or separate processes initiated outside of the conversation workflow.

SUMMARY

This summary is provided to introduce a variety of concepts in a simplified form that is further disclosed in the detailed description of the embodiments. This summary is not intended to identify key or essential inventive concepts of the claimed subject matter, nor is it intended to determine the scope of the claimed subject matter.

A computer-implemented system and method enables real-time healthcare transaction processing by converting ambient clinical speech into actionable, structured data. The system passively listens to conversations between physicians and patients using one or more microphones embedded in a computing device, such as a smartphone or tablet, and converts the captured audio into text using a speech recognition engine. The conversation initiates queries or transactions automatically without the use of direct prompts by analyzing the transcribed text using natural language processing to identify clinical intents that represent transaction opportunities, such as prescribing a medication, ordering a diagnostic procedure, or recommending a specialist referral.

Once a clinical intent is identified, the system standardizes it into a structured query format suitable for internal querying or transmission to external systems, such as systems of medical insurance carriers. These structured transmissions include relevant details such as patient demographics, diagnosis codes, and procedure or medication identifiers. The system transmits the query over a secure network and receives real-time responses from external systems, which may include information such as eligibility for or automatic enrollment into financial assistance programs (i.e. drug assistance programs), insurance coverage status, cost estimates, formulary alternatives, or prior authorization requirements with subsequent submission of the prior authorization request itself. The response is displayed in real-time to the physician or patient during the clinical encounter, enabling informed decision-making at the point of care.

The disclosed system operates passively and without requiring manual intervention by the healthcare provider. Unlike conventional systems that focus on documentation or require manual queries to external databases or direct voice prompts, the disclosed system integrates both clinical speech interpretation and transaction execution. It leverages machine learning models trained on healthcare data to detect relevant transaction events and initiate queries automatically, reducing administrative burden and expediting workflows that are often delayed by follow-up processes.

The system includes modular components, such as a speech recognition engine, a natural language processing module, a query generator, a communications interface, and a user interface module. These components function together to interpret live speech, generate structured queries, and relay queried or transactional data directly into the clinical conversation. In the insurance example, covered alternatives can be presented in real-time if certain treatments are not covered, allowing providers to proceed with informed consent or override recommendations when appropriate.

In addition to providing immediate transaction feedback, the system supports secure data retention and audit logging by storing the clinical intents and corresponding external system responses in a patient record repository. By bridging the gap between clinical conversations and healthcare administration systems, the disclosed technology transforms verbal interactions into automated transactions, improving the speed and accuracy of healthcare decision-making and administrative follow-through.

Other illustrative variations within the scope of the invention will become apparent from the detailed description provided hereinafter. The detailed description and enumerated variations, while disclosing optional variations, are intended for purposes of illustration only and are not intended to limit the scope of the invention.

BRIEF DESCRIPTION OF THE DRAWINGS

A more complete understanding of the embodiments, and the attendant advantages and features thereof, will be more readily understood by references to the following detailed description when considered in conjunction with the accompanying drawings wherein:

FIG. 4 illustrates an example flowchart of a computer-implemented method for real-time healthcare transaction processing based on ambient clinical audio, according to some embodiments;

DETAILED DESCRIPTION

Figure 1:
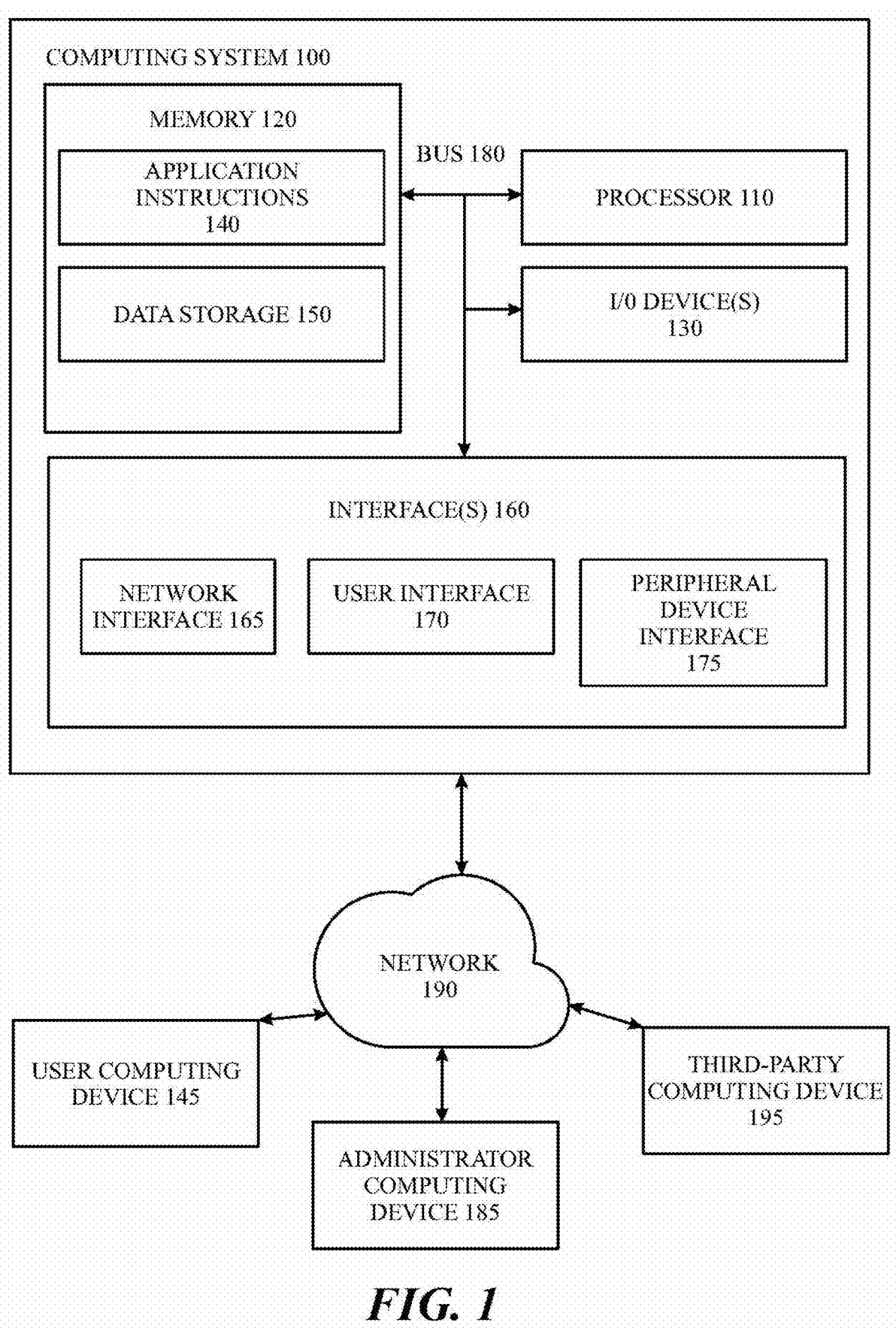
FIG. 1 illustrates a system architecture diagram, according to some embodiments.

The specific details of the single embodiment or variety of embodiments described herein are set forth in this application. Any specific details of the embodiments described herein are used for demonstration purposes only, and no unnecessary limitation(s) or inference(s) are to be understood or imputed therefrom.

Before describing exemplary embodiments in detail, it is noted that the embodiments reside primarily in combinations of components related to devices and systems. Accordingly, the device components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

A system for real-time healthcare transaction processing may include one or more computing devices that receive, interpret, and act on ambient clinical speech. A computing device may include at least one microphone configured to capture audio from a physical environment, such as a physician-patient consultation in a clinical setting, including naturally occurring conversations between a physician and a patient during a consultation, without requiring directed speech or manual activation of the system. The microphone may be integrated into a smartphone, tablet, laptop, desktop workstation, or standalone IoT device positioned in the room. The captured audio may include conversational speech involving treatment plans, diagnoses, or orders for procedures, medications, or tests.

The computing device may include a processor in communication with a memory and a set of software modules. One such module may be a speech recognition engine configured to convert captured audio into a text transcript. This engine may apply acoustic modeling and language modeling techniques to detect speech patterns, phonemes, and contextual word usage. In some implementations, the speech recognition engine may run locally on the device, or alternatively, transmit the audio data to a remote server or cloud-based system for processing using pre-trained neural network models optimized for medical vocabulary and dialogue.

Once a transcript is generated, a natural language processing (NLP) module may analyze the text to identify clinical intents. This NLP module may use parsing, tokenization, part-of-speech tagging, and named entity recognition to isolate phrases or expressions that indicate a healthcare transaction. The clinical intents may correspond to actions such as initiating a prescription, ordering a diagnostic procedure, or recommending a specialist referral. In some embodiments, the NLP module may include a classifier trained on annotated datasets comprising physician speech labeled by action type. Transformer-based architectures such as bidirectional encoder representations from transformers (BERT) or generative pre-trained transformer (GPT) models fine-tuned on electronic health record (EHR) data may be used to detect intent with high accuracy.

Once the system identifies a clinical intent, a query generator module may construct a structured query in a machine-readable format. The query may include metadata such as patient demographic information, diagnosis codes (e.g., ICD-10), medication identifiers (e.g., NDC), or procedure codes (e.g., CPT). The structure of the query may follow healthcare data standards, such as the HL7 FHIR (Fast Healthcare Interoperability Resources) specification. Mapping between detected phrases and FHIR-compliant data fields may be handled by a rule-based system or trained encoder-decoder models.

The structured query may then be transmitted to a third-party system, such as an insurance provider's API or web-based gateway. A communications module may manage this transmission using encrypted network protocols (e.g., HTTPS with TLS). The communications module may authenticate using credentials stored securely on the computing device and may use retry logic or timeout mechanisms to ensure the query completes in near real-time, such as within five seconds of initiating the request. In some embodiments, the communications module may also support requesting additional data such as prior claims history or formulary alternatives.

A response received from the third-party insurance system may contain details such as whether a medication or service is covered under a patient's plan, the estimated out-of-pocket cost, applicable deductibles, the necessity of prior authorization, recommended alternatives, or a prior authorization request itself. These results may be passed to a user interface (UI) module configured to render the information on a display. The UI module may include logic for highlighting key data fields, showing visual indicators of coverage status, and presenting alternative treatments when applicable. In some configurations, the UI may display options together, showing comparisons of covered versus non-covered treatments or medications, and may allow the physician to override system recommendations or document patient consent for a selected treatment path.

To suppress irrelevant or redundant queries, the system may include a context monitoring module that evaluates the clinical context before allowing a query to be generated. The context monitoring module may use rules, probabilistic thresholds, or context-aware filters to prevent non-actionable dialogue from triggering external communication. For example, a discussion about general medical history may be excluded, whereas statements involving current care plans may be flagged for processing.

Data retention may be handled by a secure storage module or a connection to a backend database that logs the structured queries, the system's interpretation of intent, and the external system responses received. Access to this data may be role-based and may follow HIPAA-compliant storage and encryption standards. In some implementations, failed or rejected queries may be logged separately to support reporting and system auditing.

A non-transitory computer-readable storage medium may store software instructions that, when executed by a processor, cause the system to perform the aforementioned steps. These instructions may be divided across modules and subroutines responsible for data capture, interpretation, transformation, communication, and display. The software may operate as a cloud-based application, a local executable, or a hybrid system depending on deployment requirements. In some configurations, the software may include logic to determine the urgency of each detected clinical transaction and prioritize outbound communications accordingly, especially in cases where multiple actions are being processed in parallel during a single encounter.

The graphical user interface may include a visual hierarchy that categorizes external system responses using elements such as color-coding (e.g., green for covered, yellow for conditional, red for not covered), a list of alternatives, and confirmation buttons for provider input. The interface may be customized for different clinical environments and devices, including desktop displays in physician offices or mobile layouts for handheld tablets.

The system may be configured to operate continuously in the background during patient consultations, listening passively for trigger phrases or transaction cues without requiring direct user input. In this passive mode, the system may also buffer audio to a temporary cache, discarding unneeded segments unless a transaction intent is detected. In active modes, the provider may optionally invoke the system manually using voice commands or touch interfaces to confirm or initiate specific workflows.

The described system may reduce latency between clinical decision-making and administrative execution by linking real-time speech processing with healthcare data infrastructure. Through integration of automated transcription, clinical language modeling, structured query generation, and data transmission to external systems, the system may provide a responsive tool for aligning patient care decisions with real-time payer data.

Various implementations of the invention involve the technical field of computer-based healthcare management through real-time speech-to-transaction processing including receiving real-time ambient audio input during a clinical encounter; transcribing the ambient audio into natural language text using speech recognition of naturally occurring conversations between a physician and a patient during a consultation, without requiring directed speech or manual activation of the system; detecting one or more clinical transaction intents from the natural language text using machine learning-based natural language understanding; generating one or more structured queries based on the clinical transaction intents; communicating the structured queries to an external healthcare administration system; receiving transaction data in response to the structured queries; and causing a graphical user interface to present the transaction data to at least one clinical participant during the clinical encounter, and are therefore necessarily rooted in computer technology. For example, the aforementioned steps are inherently computer-based and cannot be performed in the human mind. The present invention amounts to more than merely implementing the generic computer as a tool to gather, analyze, and output data because the steps of the present method, system, or product improve the computer-based healthcare management through real-time speech-to-transaction processing by bridging the gap between clinical conversations and healthcare administrative systems by automating the conversion of speech into structured queries and transactions, thereby reducing administrative burden while improving point-of-care decision-making through immediate access to critical information. Additionally, the steps of the present invention would be impossible to accomplish on pen and paper due to the volume of data being communicated and received over a network in real-time. In particular, the speed at which the steps of the present invention occur to effectuate the disclosed method, system, or product would involve large-scale, continuous wireless communication of such data. That is, the steps of the present method, system, or product are impossible to accomplish on pen and paper, cannot be accomplished as a method of organizing human activity, and amount to significantly more than merely gathering, analyzing, and outputting data.

Implementations of the present invention include implementing (executing, running, or deploying) one or more artificial intelligence models on a computing device wherein the computing device executes the artificial intelligence model's algorithms and mathematical functions on computer hardware using machine learning libraries. The computing device implements the artificial intelligence model when it performs tasks like training, making predictions, applying the model to data, decision-making, classification, or generating outputs based on inputs. In particular, the speed at which an artificial intelligence model analyzes and transforms data to effectuate the disclosed method, system, or product would involve large-scale, continuous transformation of such data. As such, the present invention would be impossible to accomplish on pen and paper or in the human mind due to the volume of data being analyzed and transformed by the artificial intelligence model.

FIG. 1 illustrates an example of a computer system 100 that may be utilized to execute various procedures, including the processes described herein. The computer system 100 comprises a standalone computer or mobile computing device, a mainframe computer system, a workstation, a network computer, a desktop computer, a laptop, an API-based service, or the like. The computer system 100 can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive).

In some embodiments, the computer system 100 includes one or more processors 110 coupled to a memory 120 through a system bus 180 that couples various system components, such as an input/output (I/O) devices 130, to the processors 110. The bus 180 may be any of several types of bus structures including a memory bus or memory controller, a peripheral bus, and a local bus using any of a variety of bus architectures. For example, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

In some embodiments, the computer system 100 includes one or more input/output (I/O) devices 130, such as video device(s) (e.g., a camera), audio device(s), and display(s) are in operable communication with the computer system 100. In some embodiments, similar I/O devices 130 may be separate from the computer system 100 and may interact with one or more nodes of the computer system 100 through a wired or wireless connection, such as over a network interface.

Processors 110 suitable for the execution of computer readable program instructions include both general and special purpose microprocessors and any one or more processors of any digital computing device. For example, each processor 110 may be a single processing unit or a number of processing units and may include single or multiple computing units or multiple processing cores. The processor(s) 110 can be implemented as one or more microprocessors, microcomputers, microcontrollers, digital signal processors, central processing units, state machines, logic circuitries, and/or any devices that manipulate signals based on operational instructions. For example, the processor(s) 110 may be one or more hardware processors and/or logic circuits of any suitable type specifically programmed or configured to execute the algorithms and processes described herein. The processor(s) 110 can be configured to fetch and execute computer readable program instructions stored in the computer-readable media, which can program the processor(s) 110 to perform the functions described herein.

In this disclosure, the term "processor" can refer to substantially any computing processing unit or device, including single-core processors, single-processors with software multithreading execution capability, multi-core processors, multi-core processors with software multithreading execution capability, multi-core processors with hardware multithread technology, parallel platforms, and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures, such as molecular and quantum-dot based transistors, switches, and gates, to optimize space usage or enhance performance of user equipment. A processor can also be implemented as a combination of computing processing units.

In some embodiments, the memory 120 includes computer-readable application instructions 140, configured to implement certain embodiments described herein, and a database 150, comprising various data accessible by the application instructions 140. In some embodiments, the application instructions 140 include software elements corresponding to one or more of the various embodiments described herein. For example, application instructions 140 may be implemented in various embodiments using any desired programming language, scripting language, or combination of programming and/or scripting languages (e.g., Android, C, C++, C#, JAVA, JAVASCRIPT, PERL, etc.).

In this disclosure, terms "store," "storage," "data store," data storage," "database," and substantially any other information storage component relevant to operation and functionality of a component are utilized to refer to "memory components," which are entities embodied in a "memory," or components comprising a memory. Those skilled in the art would appreciate that the memory and/or memory components described herein can be volatile memory, nonvolatile memory, or both volatile and nonvolatile memory. Nonvolatile memory can include, for example, read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include, for example, RAM, which can act as external cache memory. The memory and/or memory components of the systems or computer-implemented methods can include the foregoing or other suitable types of memory.

Generally, a computing device will also include or be operatively coupled to receive data from or transfer data to, or both, one or more mass data storage devices; however, a computing device need not have such devices. The computer readable storage medium (or media) can be a tangible device that can retain and store instructions for use by an instruction execution device. The computer readable storage medium can be, for example, an electronic storage device, a magnetic storage device, an optical storage device, an electromagnetic storage device, a semiconductor storage device, or any suitable combination of the foregoing. A non-exhaustive list of more specific examples of the computer readable storage medium can include: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. In this disclosure, a computer readable storage medium is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

In some embodiments, the steps and actions of the application instructions 140 described herein are embodied directly in hardware, in a software module executed by a processor, or in a combination of the two. A software module may reside in RAM, flash memory, ROM memory, EPROM memory, EEPROM memory, registers, a hard disk, a removable disk, a CD-ROM, or any other form of storage medium known in the art. An exemplary storage medium may be coupled to the processor 110 such that the processor 110 can read information from, and write information to, the storage medium. In the alternative, the storage medium may be integrated into the processor 110. Further, in some embodiments, the processor 110 and the storage medium may reside in an Application Specific Integrated Circuit (ASIC). In the alternative, the processor and the storage medium may reside as discrete components in a computing device. Additionally, in some embodiments, the events or actions of a method or algorithm may reside as one or any combination or set of codes and instructions on a machine-readable medium or computer-readable medium, which may be incorporated into a computer program product.

In some embodiments, the application instructions 140 for carrying out operations of the present disclosure can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The application instructions 140 can execute entirely on the user's computer, partly on the user's computer, as a stand-alone software package, partly on the user's computer and partly on a remote computer, or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present disclosure.

In some embodiments, the application instructions 140 can be downloaded to a computing/processing device from a computer readable storage medium, or to an external computer or external storage device via a network 190. A network adapter card or network interface in each computing/processing device receives computer readable program instructions from the network and forwards the computer readable application instructions 140 for storage in a computer readable storage medium within the respective computing/processing device.

In some embodiments, the computer system 100 includes one or more interfaces 160 that allow the computer system 100 to interact with other systems, devices, or computing environments. In some embodiments, the computer system 100 comprises a network interface 165 to communicate with a network 190. In some embodiments, the network interface 165 is configured to allow data to be exchanged between the computer system 100 and other devices attached to the network 190, such as other computer systems, or between nodes of the computer system 100. In various embodiments, the network interface 165 may support communication via wired or wireless general data networks, such as any suitable type of Ethernet network, for example, via telecommunications/telephony networks such as analog voice networks or digital fiber communications networks, via storage area networks such as Fiber Channel SANs, or via any other suitable type of network and/or protocol. Other interfaces include the user interface 170 and the peripheral device interface 175.

In some embodiments, the network 190 corresponds to a local area network (LAN), wide area network (WAN), the Internet, a direct peer-to-peer network (e.g., device to device Wi-Fi, Bluetooth, etc.), and/or an indirect peer-to-peer network (e.g., devices communicating through a server, router, or other network device). The network 190 can comprise copper transmission cables, optical transmission fibers, wireless transmission, routers, firewalls, switches, gateway computers and/or edge servers. The network 190 can represent a single network or multiple networks. In some embodiments, the network 190 used by the various devices of the computer system 100 is selected based on the proximity of the devices to one another or some other factor. For example, when a first user device and second user device are near each other (e.g., within a threshold distance, within direct communication range, etc.), the first user device may exchange data using a direct peer-to-peer network. But when the first user device and the second user device are not near each other, the first user device and the second user device may exchange data using a peer-to-peer network (e.g., the Internet). The Internet refers to the specific collection of networks and routers communicating using an Internet Protocol ("IP") including higher level protocols, such as Transmission Control Protocol/Internet Protocol ("TCP/IP") or the Uniform Datagram Packet/Internet Protocol ("UDP/IP").

Any connection between the components of the system may be associated with a computer-readable medium. For example, if software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. As used herein, the terms "disk" and "disc" include compact disc (CD), laser disc, optical disc, digital versatile disc (DVD), floppy disk, and Blu-ray disc; in which "disks" usually reproduce data magnetically, and "discs" usually reproduce data optically with lasers. Combinations of the above should also be included within the scope of computer-readable media. In some embodiments, the computer-readable media includes volatile and nonvolatile memory and/or removable and non-removable media implemented in any type of technology for storage of information, such as computer-readable instructions, data structures, program modules, or other data. Such computer-readable media may include RAM, ROM, EEPROM, flash memory or other memory technology, optical storage, solid state storage, magnetic tape, magnetic disk storage, RAID storage systems, storage arrays, network attached storage, storage area networks, cloud storage, or any other medium that can be used to store the desired information and that can be accessed by a computing device. Depending on the configuration of the computing device, the computer-readable media may be a type of computer-readable storage media and/or a tangible non-transitory media to the extent that when mentioned, non-transitory computer-readable media exclude media such as energy, carrier signals, electromagnetic waves, and signals per se.

In some embodiments, the system is world-wide-web (www) based, and the network server is a web server delivering HTML, XML, etc., web pages to the computing devices. In other embodiments, a client-server architecture may be implemented, in which a network server executes enterprise and custom software, exchanging data with custom client applications running on the computing device.

In some embodiments, the system can also be implemented in cloud computing environments. In this context, "cloud computing" refers to a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

As used herein, the term "add-on" (or "plug-in") refers to computing instructions configured to extend the functionality of a computer program, where the add-on is developed specifically for the computer program. The term "add-on data" refers to data included with, generated by, or organized by an add-on. Computer programs can include computing instructions, or an application programming interface (API) configured for communication between the computer program and an add-on. For example, a computer program can be configured to look in a specific directory for add-ons developed for the specific computer program. To add an add-on to a computer program, for example, a user can download the add-on from a website and install the add-on in an appropriate directory on the user's computer.

In some embodiments, the computer system 100 may include a user computing device 145, an administrator computing device 185 and a third-party computing device 195 each in communication via the network 190. The user computing device 145 may be utilized by a user to interact with the various functionalities of the system. The administrator computing device 185 is utilized by an administrative user to moderate content and to perform other administrative functions. The third-party computing device 195 may be utilized by third parties to receive communications from the user computing device, transmit communications to the user via the network, and otherwise interact with the various functionalities of the system.

Figure 2:
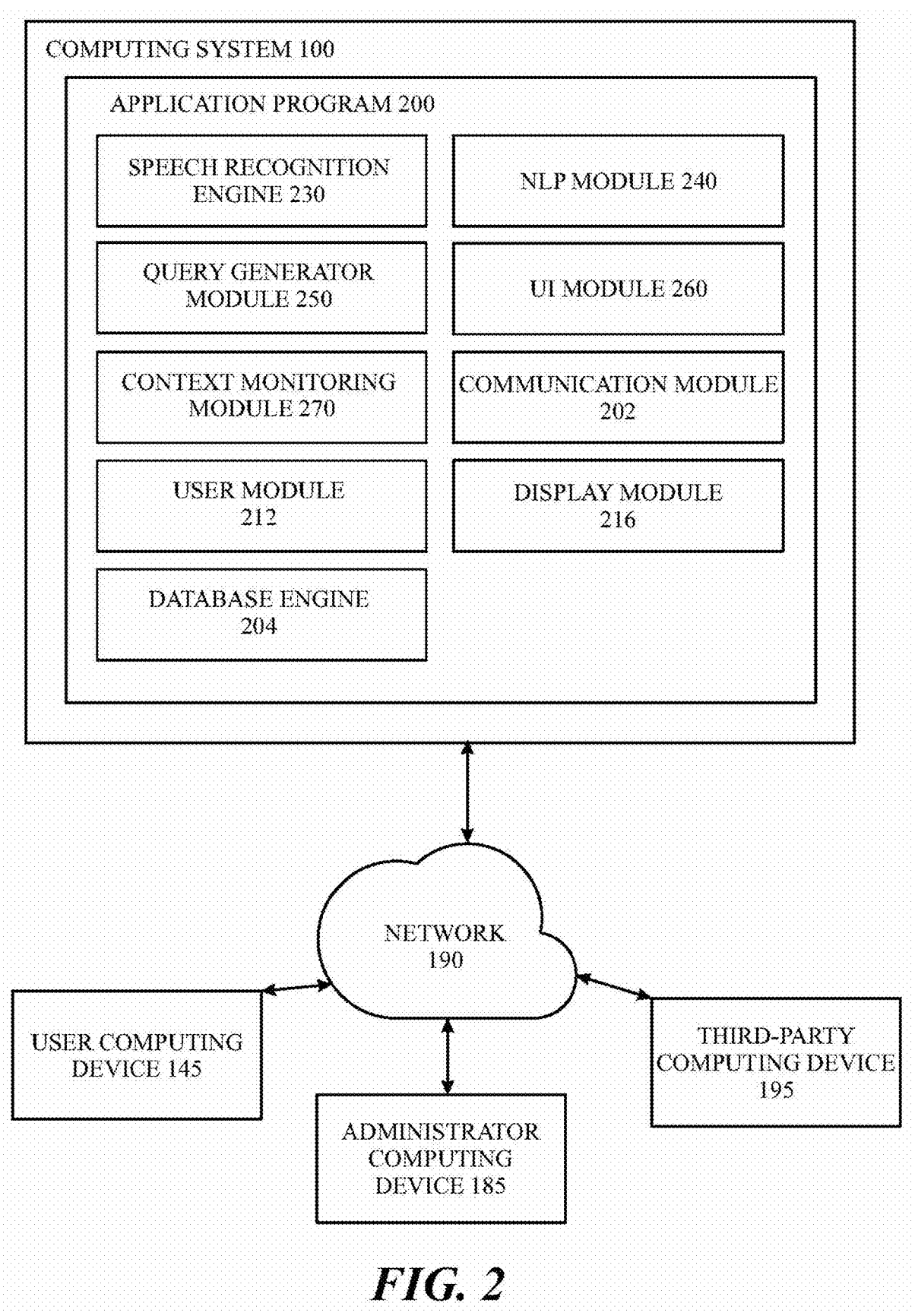
FIG. 2 illustrates an application program and modules in communication with the computing system, according to some embodiments.

FIG. 2 illustrates an example computer architecture for the application program 200 operated via the computing system 100. The computer system 100 comprises several modules and engines configured to execute the functionalities of the application program 200, and a database engine 204 configured to facilitate how data is stored and managed in one or more databases. In particular, FIG. 2 is a block diagram showing the modules and engines needed to perform specific tasks within the application program 200.

Referring to FIG. 2, the computing system 100 operating the application program 200 comprises one or more modules having the necessary routines and data structures for performing specific tasks, and one or more engines configured to determine how the platform manages and manipulates data. In some embodiments, the application program 200 comprises one or more of a speech recognition engine 230, an NLP module 240, a query generator module 250, a UI module 260, a context monitoring module 270, a communication module 202, a database engine 204, a user module 212, and a display module 216.

In some embodiments, the speech recognition engine 230 is configured to receive ambient audio input captured via one or more microphones positioned within a clinical environment and convert the spoken dialogue into a machine-readable text transcript. The audio input may include naturally occurring conversations between a physician and a patient during a consultation, without requiring directed speech or manual activation of the system. The speech recognition engine 230 may operate continuously or within predefined session windows, capturing relevant audio segments in real time.

The speech recognition engine 230 may include or interface with an acoustic model trained to identify phonemes and other sound units associated with medical terminology. It may also include a language model configured to predict and construct contextually accurate phrases based on recognized word sequences. These models may be implemented using neural network architectures such as convolutional neural networks (CNNs) or recurrent neural networks (RNNs), or more recent architectures such as transformers. In some implementations, the engine may utilize domain-specific corpora, including clinical notes, electronic health record data, and transcribed patient encounters, to improve recognition accuracy within the healthcare domain.

To enhance performance in noisy clinical environments, the speech recognition engine 230 may apply pre-processing techniques such as echo cancellation, noise suppression, and voice activity detection to isolate relevant speech. The system may segment the audio into time-stamped utterances, tag them by speaker identity where possible, and discard silent or irrelevant portions.

After processing, the speech recognition engine 230 may produce a structured transcript of the physician-patient conversation. This transcript may be forwarded to downstream modules, such as a natural language processing module, for further analysis. In some embodiments, the speech recognition engine 230 may be implemented locally on a computing device with sufficient processing capabilities or remotely on a cloud-based infrastructure, depending on the deployment configuration. The engine may operate synchronously to provide near-instantaneous results or asynchronously in scenarios where slight latency is acceptable.

By enabling passive and accurate conversion of clinical speech to text, the speech recognition engine 230 supports real-time identification of actionable healthcare intents and contributes to automating downstream healthcare transaction workflows.

In some embodiments, the NLP module 240 is configured to receive a text transcript generated from ambient clinical speech and analyze the content to identify clinical transaction intents. The transcript may include naturally spoken dialogue from physician-patient interactions and may contain informal phrasing, incomplete sentences, or domain-specific terminology. The NLP module 240 processes this unstructured language data to detect expressions that indicate a proposed clinical action, such as prescribing a medication, ordering imaging, or recommending a procedure.

The NLP module 240 may tokenize the input text and apply syntactic and semantic parsing to derive contextual relationships between terms. It may utilize rule-based systems or statistical models to tag entities such as drug names, diagnostic tests, procedure types, and medical conditions. In some implementations, the NLP module 240 may use named entity recognition and dependency parsing to isolate meaningful phrases that reflect intent.

To improve accuracy and robustness, the NLP module 240 may incorporate machine learning models trained on annotated healthcare datasets. These models may include transformer-based architectures, such as those built using bidirectional attention mechanisms, that have been fine-tuned on clinical text corpora. The models may be configured to classify segments of the transcript according to a predefined set of intent categories, such as "prescription," "diagnostic request," or "referral," and to extract relevant parameters needed for downstream processing.

The NLP module 240 may also be configured to disambiguate ambiguous expressions using contextual cues. For example, it may determine whether a physician's mention of a medication reflects an active prescription recommendation or a general discussion of treatment options. This contextual evaluation may involve co-reference resolution and time-sensitive filtering to focus only on current or near-future intended actions.

Once the clinical intent is identified, the NLP module 240 may output a structured representation of the detected intent, including its type and associated parameters, such as medication name, dosage, imaging modality, or target body region. This structured data may be passed to a query generator module for further formatting and submission to an external system.

In some embodiments, the NLP module 240 may operate in real time and process each segment of conversation as it becomes available from the speech recognition engine. The NLP module 240 may also be configured to continuously update its classification results as more contextual data is received, allowing it to revise previously inferred intents when new information suggests a different interpretation.

By extracting actionable clinical intents from natural speech, the NLP module 240 enables the system to initiate downstream workflows without requiring manual entry, facilitating automated external system queries and other administrative actions directly from conversational input.

In some embodiments, the query generator module 250 is configured to receive structured clinical intent data from the NLP module and transform that data into a query format suitable for submission to an external healthcare administration system, such as an insurance database or third-party payer platform. The input may include metadata extracted from conversational speech, such as the identified clinical intent type, associated medical terminology, patient identifiers, and any contextual details relevant to the proposed healthcare transaction.

The query generator module 250 may map each element of the structured clinical intent to standardized fields recognized by external systems. These fields may include healthcare industry-standard identifiers, such as ICD-10 codes for diagnoses, CPT codes for procedures, and NDC codes for medications. In some configurations, the query generator module 250 may use a local or cloud-based lookup table or terminology mapping service to convert plain-language terms into standardized code values.

Once the relevant parameters are encoded, the query generator module 250 may assemble them into a formatted data payload that conforms to a predefined schema. In some embodiments, the query generator module 250 may produce queries formatted according to HL7 FHIR protocols, which define structured resources for transmitting clinical and administrative data. For example, a detected prescription intent may be encoded as a FHIR Medication Request resource with embedded references to medication code, dosage instruction, and patient information.

The query generator module 250 may also include logic for conditionally adding fields based on the transaction type. For instance, a query involving a diagnostic imaging request may include body part, modality, and medical necessity justification, while a prior authorization query may include a provider NPI, estimated service date, and reason for urgency. The query generator module 250 may also support the inclusion of patient demographic data, policy numbers, and coverage plan information if that data is available from connected EHR systems or patient registration input.

To ensure compatibility with external systems, the query generator module 250 may validate the structured query format against expected schemas or specification rules provided by the external system. The query generator module 250 may perform schema validation, check for required fields, and sanitize data to prevent errors during transmission. In some configurations, the query generator module 250 may prepare multiple query formats simultaneously if redundancy or cross-system interoperability is needed.

After generation, the completed structured query is passed to the communications module for secure transmission over a network. In some embodiments, the query generator module 250 may maintain a log of generated queries along with timestamps, identifiers, and summary content to support traceability and auditing.

By translating clinical intent into machine-readable, standards-based queries, the query generator module 250 allows the system to execute healthcare transactions in real time without manual intervention, thereby streamlining processes such as coverage verification, cost estimation, and authorization submission.

In some embodiments, the UI module 260 is configured to present transaction data, such as insurance transaction data, to a physician, patient, or other authorized user in real time during a clinical encounter. The UI module 260 may receive structured insurance response data from the communications module following submission of a query to a third-party healthcare administration system. This data may include information such as medication coverage status, service cost estimates, prior authorization requirements, or alternative options available under the patient's health plan.

The UI module 260 may include routines for parsing the response payload and extracting key data elements for display. The UI module 260 may format the information into a human-readable presentation that supports rapid decision-making at the point of care. In some embodiments, the UI module 260 may render this data within a graphical user interface that is accessible on a computing device such as a tablet, smartphone, or desktop terminal located in the exam room or connected remotely through a secure session.

To enhance usability, the UI module 260 may apply visual design principles such as color-coding, iconography, and layout grouping. For example, responses indicating full coverage may be displayed with green indicators, while uncovered or conditionally covered items may appear in red or yellow, respectively. The UI module 260 may also support side-by-side comparisons of covered and non-covered alternatives, enabling physicians to evaluate substitute medications, procedures, or tests when initial options are denied or restricted.

In some embodiments, the UI module 260 may provide interactive elements that allow users to navigate through multiple sections of the response data. For instance, a physician may expand or collapse panels showing prior authorization forms, cost-sharing breakdowns, or step therapy requirements. The UI module 260 may also include buttons or inputs for acknowledging results, overriding recommendations, or initiating a manual override or follow-up workflow.

The UI module 260 may integrate with a local display stack or operate within a web-based interface, depending on system configuration. The UI module 260 may refresh content automatically as new responses are received from the external system, or it may update periodically based on polling intervals or user commands. In some implementations, it may support real-time filtering or prioritization, such as highlighting urgent coverage conflicts or cost-prohibitive options that require immediate action.

To support clinical documentation or the initiation of a transaction, the UI module 260 may optionally transmit user selections, annotations, or confirmations back to a local database or EHR integration layer. This may include logging the time of display, the content viewed, and any interaction captured through the interface.

By transforming structured external data into actionable visual content, the UI module 260 enables healthcare providers and patients to make informed decisions during the clinical consultation, without exiting the workflow or requiring separate systems to access administrative data.

In some embodiments, the context monitoring module 270 is configured to evaluate the content and timing of physician-patient dialogue to determine whether a detected utterance warrants the generation of a healthcare transaction or query. The context monitoring module 270 may operate in coordination with the NLP module and speech recognition engine, analyzing incoming transcribed text for contextual relevance before allowing downstream modules to proceed with query generation and submission.

The context monitoring module 270 may apply a combination of rule-based logic and probabilistic models to assess whether a statement made during the conversation is associated with an actionable clinical decision. For example, it may determine whether the physician's mention of a medication refers to a new prescription, a general discussion of drug efficacy, or a historical reference to past treatment. Only those utterances that meet a defined threshold for clinical immediacy or transactional relevance may trigger further processing.

To achieve this, the context monitoring module 270 may use temporal filters to assess the timing of a statement in relation to surrounding utterances, evaluating whether the dialogue contains confirming language or intent indicators, such as "we'll start you on," "I'm ordering," or "let's get you scheduled for." In some configurations, the context monitoring module 270 may incorporate natural language classifiers trained on labeled datasets to predict the likelihood that a given phrase corresponds to a billable or administratively actionable event.

The context monitoring module 270 may also suppress duplicate transaction triggers that arise from repeated or elaborated statements. For example, if a physician discusses a procedure in detail across multiple utterances, the context monitoring module 270 may recognize that only a single transaction should be initiated. This helps reduce redundancy in query traffic and limits unnecessary load on external systems.

In some embodiments, the context monitoring module 270 may monitor the session as a whole and apply conversational boundary detection techniques to separate general discussion from transactional moments. It may maintain a rolling window of recent dialogue and update its assessment continuously based on new input from the speech recognition engine.

To support customization, the context monitoring module 270 may allow configuration of context rules or thresholds based on specialty, clinical setting, or institutional preferences. In some implementations, it may interface with a user preference profile or institutional policy engine to adjust sensitivity and transaction criteria.

By filtering out non-actionable or ambiguous utterances, the context monitoring module 270 helps ensure that the system initiates queries only when appropriate, improving efficiency, reducing false positives, and preserving the integrity of automated interactions with third-party systems.

In some embodiments, the communication module 202 is configured for receiving, processing, and transmitting a user command and/or one or more data streams. In such embodiments, the communication module 202 performs communication functions between various devices, including the user computing device 145 of FIG. 1, the administrator computing device 185 of FIG. 1, and a third-party computing device 195 of FIG. 1. In some embodiments, the communication module 202 is configured to allow one or more users of the system, including a third-party, to communicate with one another. In some embodiments, the communications module 202 is configured to maintain one or more communication sessions with one or more servers, the administrative computing device 185 of FIG. 1, and/or one or more third-party computing device(s) 195 of FIG. 1. In some embodiments, the communication module 202 may allow users and administrators to communicate with one another.

In some embodiments, a database engine 204 is configured to facilitate the storage, management, and retrieval of data to and from one or more storage mediums, such as the one or more internal databases described herein. In some embodiments, the database engine 204 is coupled to an external storage system. In some embodiments, the database engine 204 is configured to apply changes to one or more databases. In some embodiments, the database engine 204 comprises a search engine component for searching through thousands of data sources stored in different locations.

The user module 212 may store user preferences including the user account information, historical usage data, user personal information, and the like. The user module 212 may facilitate the creation of user's profiles for users, administrators, and others.

In some embodiments, the display module 216 is configured to display one or more graphic user interfaces, including, e.g., one or more user interfaces. In some embodiments, the display module 216 is configured to temporarily generate and display various pieces of information in response to one or more commands or operations. The various pieces of information or data generated and displayed may be transiently generated and displayed, and the displayed content in the display module 216 may be refreshed and replaced with different content upon the receipt of different commands or operations in some embodiments. In such embodiments, the various pieces of information generated and displayed in a display module 216 may not be persistently stored. The display module 216 displays information, notifications, and alerts to the user device which can be viewed and acknowledged by the user.

Figure 3:
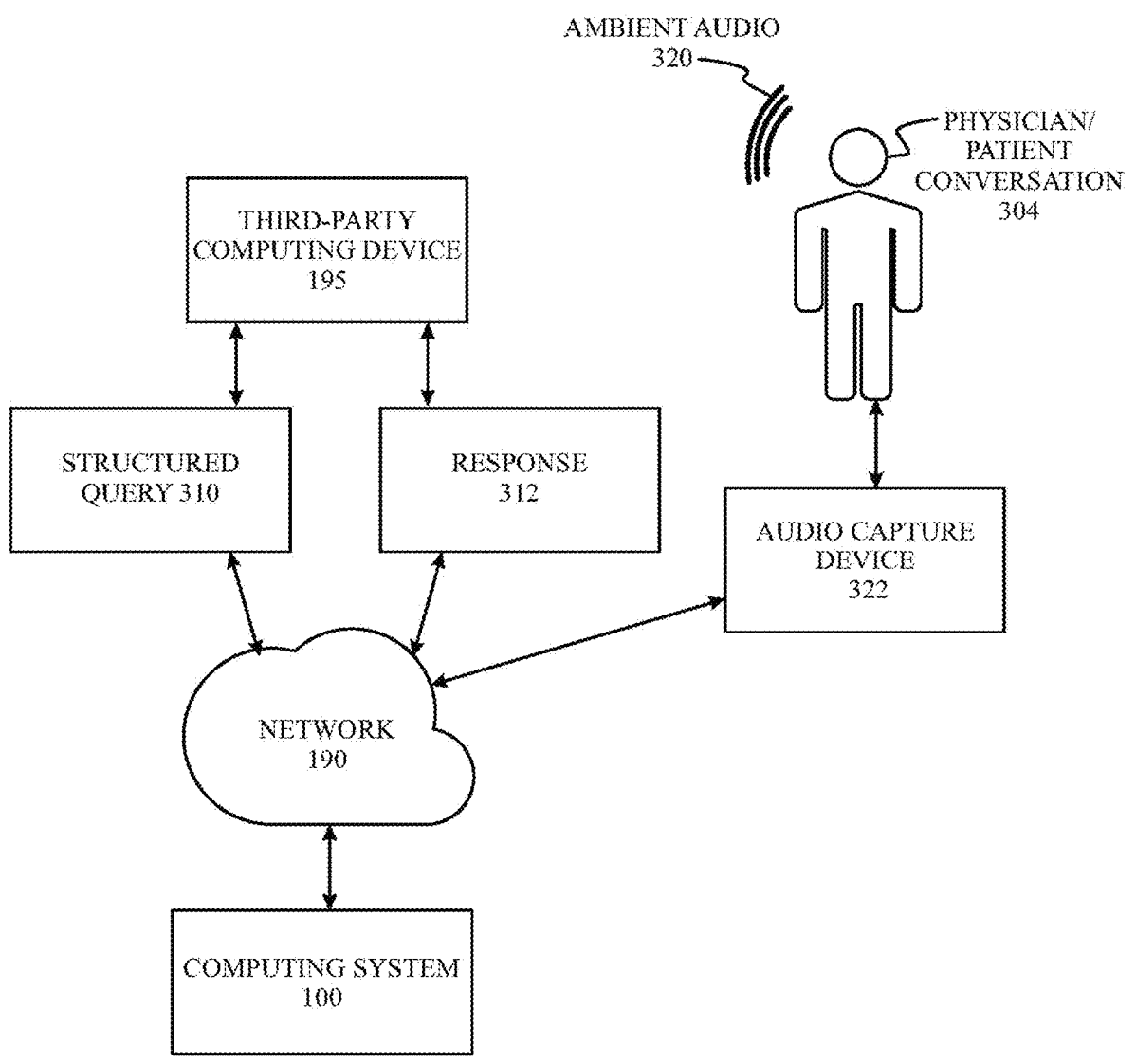
FIG. 3 illustrates an example environment in which a computing system performs real-time healthcare transaction processing based on ambient audio captured from a physician-patient conversation, according to some embodiments.

FIG. 3 illustrates an example environment in which a computing system 100 performs real-time healthcare transaction processing based on ambient audio 320 captured from a physician-patient conversation 304. As shown, an audio capture device 322, such as a microphone embedded in a smartphone, tablet, or dedicated clinical device, receives the ambient audio 320 produced during the interaction. The audio may contain naturally spoken dialogue related to treatment decisions, medication recommendations, or diagnostic requests.

The audio capture device 322 is communicatively coupled to the computing system 100 through a network 190. The computing system 100 may include or access one or more software modules (not individually shown in this figure) that transcribe the received audio into text, analyze the transcript to detect one or more clinical intents, and generate a structured query 310 corresponding to the identified transaction. The structured query 310 may include, for example, information relating to a proposed medication, diagnostic test, or medical procedure.

The structured query 310 is transmitted via the network 190 to a third-party computing device 195, which may correspond to an external insurance or administrative system. In response, the third-party computing device 195 transmits an response 312 back to the computing system 100. The response 312 may include data such as coverage status, cost information, or prior authorization requirements associated with the detected clinical intent.

As shown, both the structured query 310 and response 312 pass through the network 190 between the computing system 100 and the third-party computing device 195. The response 312 may also be routed back to the audio capture device 322 for display to the physician, patient, or other clinical staff. This architecture enables real-time analysis and feedback based on live conversations, facilitating immediate access to third-party data during the clinical encounter.

FIG. 4 illustrates an example flowchart of a computer-implemented method for real-time healthcare transaction processing based on ambient clinical audio, as described in claim 1. At step 402, the method includes receiving, via one or more microphones of a computing device, ambient audio originating from a physician-patient conversation. This audio may be captured passively during a clinical encounter without requiring user activation or structured command input. At step 404, the ambient audio is transcribed into text using a speech recognition engine. The transcription process may apply language and acoustic models adapted to medical dialogue, producing a text-based representation of the conversation in near real-time. At step 406, the transcribed text is analyzed using a natural language processing engine to identify one or more clinical intents corresponding to healthcare transactions. The NLP engine may detect language indicative of a proposed treatment, diagnostic test, medication, or other administrative action requiring follow-up. At step 408, the identified clinical intent is standardized into a structured query format. This may include converting free-text expressions into coded values using standardized data schemas such as HL7 FHIR, and populating data fields with patient and transaction-specific attributes such as diagnosis codes or medication identifiers. At step 410, the structured query is transmitted to an external system over a network to request data corresponding to the clinical intent. The query may be sent through an API or other secure communications channel. At step 412, a response is received via the computing device from the external system. The response may include information such as insurance coverage status, medication cost, or prior authorization requirements associated with the detected intent. The method further includes displaying the response in real time to at least one of the physician or the patient during the clinical encounter, enabling informed decision-making based on current administrative and financial data. FIG. 4 represents an implementation of the automated method that enables ambient speech to initiate external queries with minimal manual intervention, allowing healthcare professionals to integrate clinical decisions and administrative workflows during live interactions.

Figure 5:
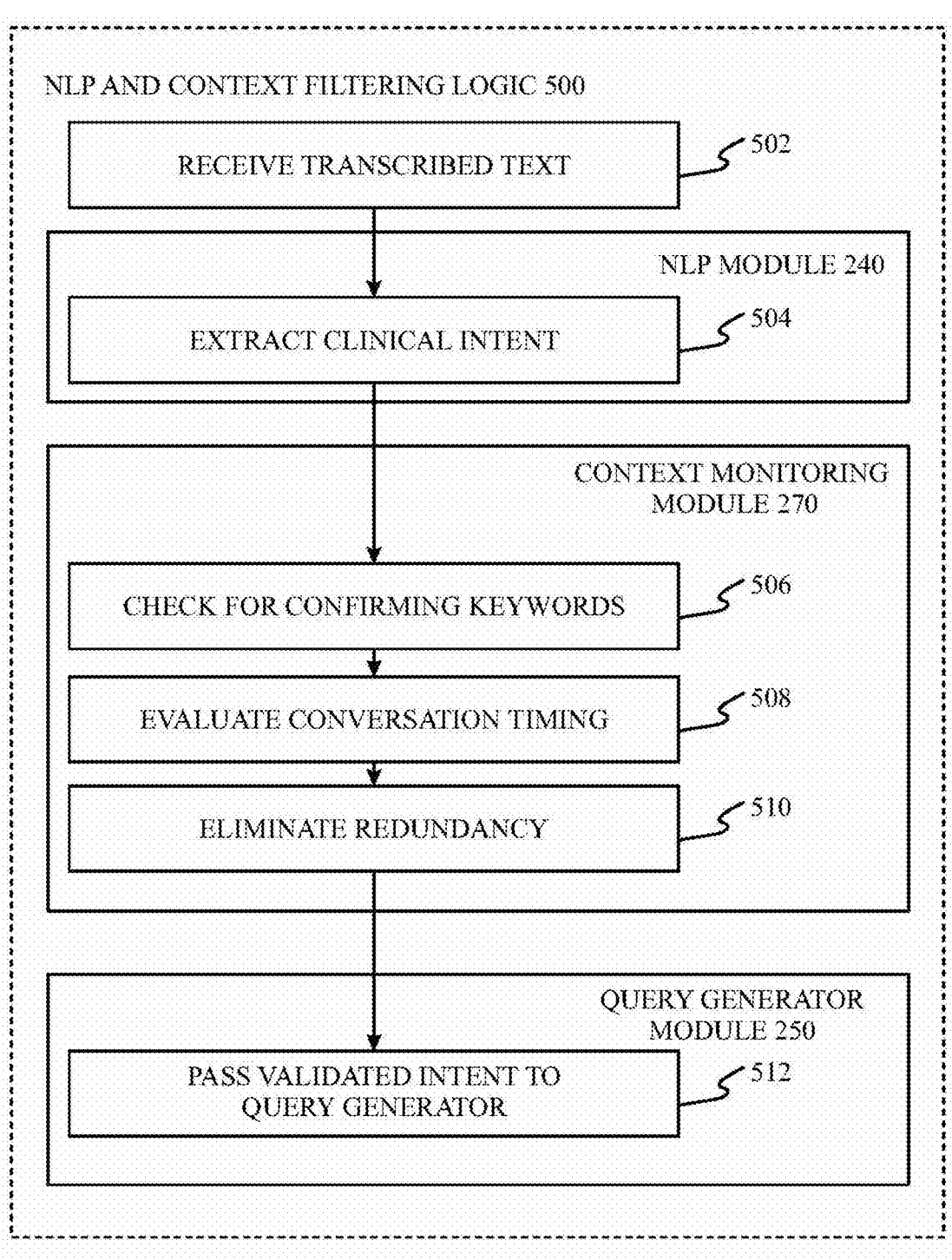
FIG. 5 illustrates an example workflow of NLP and context filtering logic for validating clinical intent prior to query generation within the system for real-time healthcare transaction processing, according to some embodiments.

FIG. 5 illustrates an example workflow of natural language processing (NLP) and context filtering logic 500 for validating clinical intent prior to query generation within the system for real-time healthcare transaction processing. At step 502, transcribed text is received by the NLP module 240. This text may be generated from ambient audio captured during a physician-patient conversation and converted to text using a speech recognition engine. The transcript includes free-form spoken language that may contain medical dialogue relevant to healthcare decisions. At step 504, the NLP module 240 analyzes the received transcript to extract a clinical intent. This may include identifying whether the physician is initiating an action such as prescribing a medication, ordering a diagnostic test, or referring the patient for a procedure. The module may use syntactic parsing, semantic classification, and entity recognition to produce a structured representation of the intent. Following extraction, the clinical intent is evaluated by the context monitoring module 270 to determine whether the intent is actionable and suitable for triggering a transaction query. At step 506, the context monitoring module 270 checks for confirming keywords or phrases within the surrounding transcript. These keywords may indicate decisiveness or confirmation of a proposed clinical action, such as "I will prescribe," "let's order," or "schedule this." At step 508, the module evaluates the timing of the utterance relative to adjacent dialogue. This temporal analysis helps determine whether the identified intent represents a current decision or a reference to a past or future event that should not trigger immediate action. At step 510, the module applies redundancy elimination logic to prevent duplicate intents from being processed. For example, if a single recommendation is mentioned in multiple ways or repeated across the conversation, the system may recognize it as one unified intent. At step 512, after passing the context validation checks, the validated intent is forwarded to the query generator module 250. This module is responsible for constructing a structured query to be sent to an external system for administrative data retrieval. This process ensures that only relevant, timely, and distinct clinical intents are passed forward for processing, thereby improving the accuracy and efficiency of the automated speech-to-transaction system. The modular interaction shown in FIG. 5 reflects the layered decision logic that precedes the generation of external queries.

Figure 6:
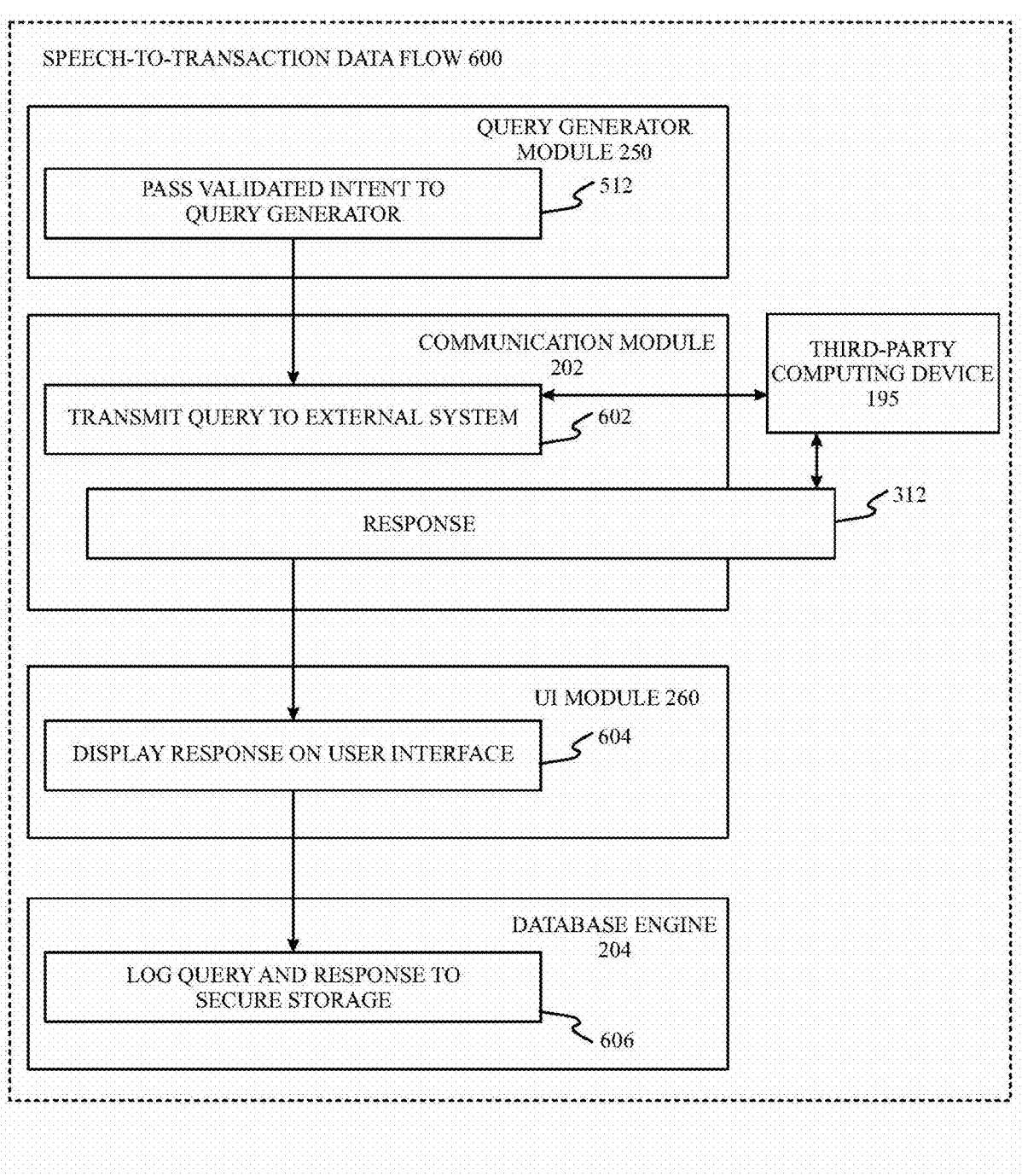
FIG. 6 illustrates an example speech-to-transaction data flow showing the sequence of operations initiated after clinical intent is validated, beginning with query generation and ending with data presentation and logging, according to some embodiments.

FIG. 6 illustrates an example speech-to-transaction data flow 600 showing the sequence of operations initiated after clinical intent is validated, beginning with query generation and ending with data presentation and logging. This figure builds upon earlier processing stages described in FIG. 5. At step 512, a validated clinical intent is passed to the query generator module 250. This module converts the validated intent into a structured query formatted for compatibility with external systems, such as an insurance provider's API. The structured query may include standardized data fields representing procedure codes, medication identifiers, patient demographics, and related metadata. At step 602, the communication module 202 transmits the structured query to a third-party computing device 195 corresponding to an external system. The communication module may initiate this request over a secure network connection, using application-level protocols and payload formats defined by healthcare interoperability standards (e.g., HL7 FHIR). The third-party computing device 195 processes the query and generates a corresponding response 312, which is transmitted back to the communication module 202. Once received, the response 312 is forwarded to the UI module 260. At step 604, the UI module 260 displays the response on a user interface accessible to at least one of the physician or patient during the clinical encounter. The user interface may present data elements such as coverage status, cost information, authorization requirements, or recommended alternatives, and may include visual formatting that aids rapid comprehension. At step 606, the database engine 204 logs the query and response to secure storage. This step may support compliance, auditability, and continuity of care by maintaining a record of healthcare transactions triggered during clinical conversations. The logged data may be indexed for retrieval and associated with patient records or encounter metadata. FIG. 6 illustrates how the system converts validated clinical speech into actionable administrative transactions, completing the end-to-end flow from ambient conversation to real-time external data integration.

Figure 7:
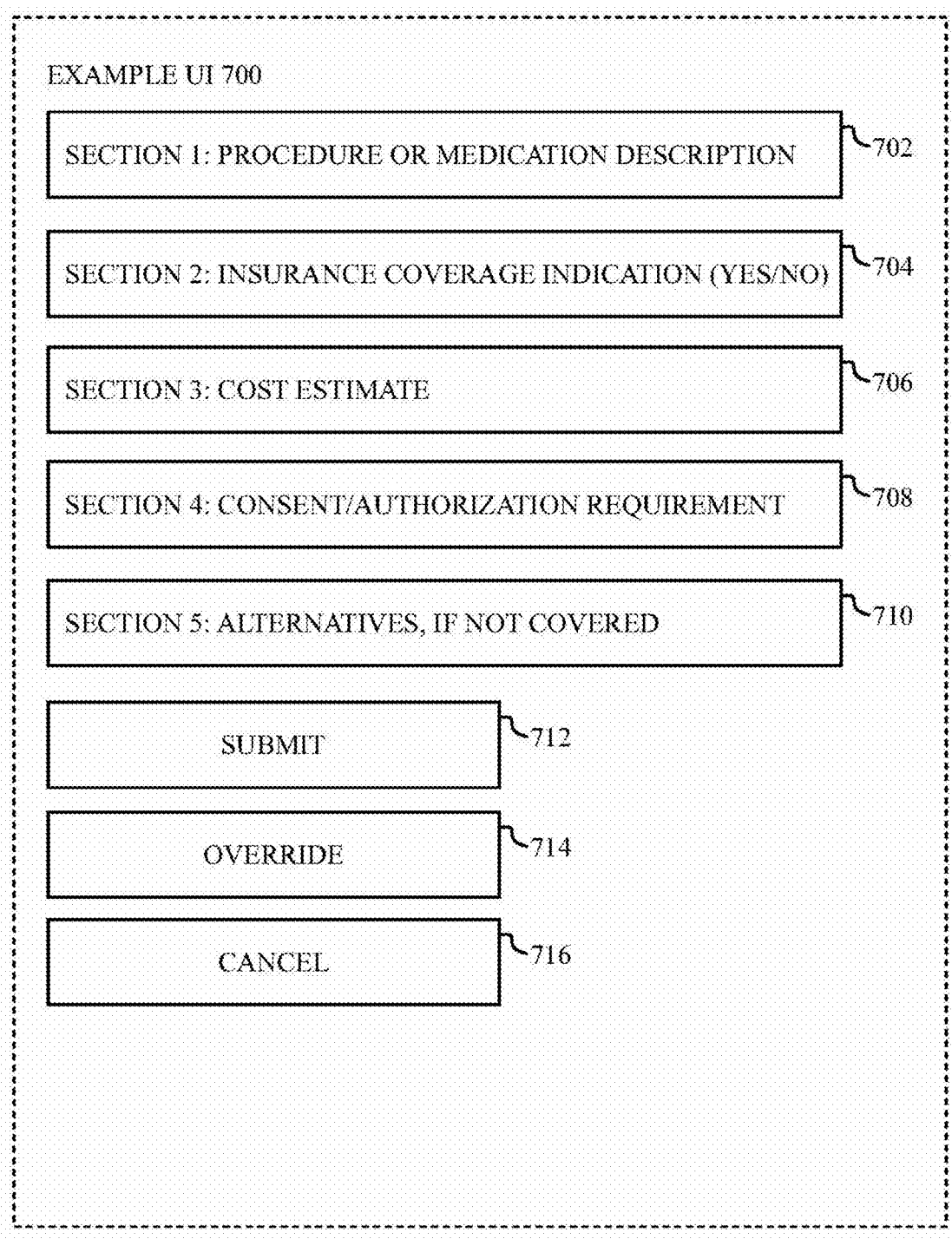
FIG. 7 illustrates an example user interface that may be generated and rendered by the UI module to display insurance-related data to a user in response to a structured transaction query initiated during a physician-patient encounter.

FIG. 7 illustrates an example user interface 700 that may be generated and rendered by the UI module to display insurance-related data to a user in response to a structured transaction query initiated during a physician-patient encounter. The interface may be accessed on a computing device such as a tablet, desktop, or mobile platform within the clinical environment. As shown, the interface includes multiple data sections corresponding to elements received in the insurance response. Section 702 presents a procedure or medication description. This section may summarize the clinical intent detected from ambient speech, such as the name of a prescribed drug or the type of diagnostic imaging ordered. Section 704 provides an insurance coverage indication, displaying whether the identified procedure or medication is covered under the patient's current insurance plan. This field may be binary (e.g., yes/no or green/yellow/red) or may include additional indicators such as conditional or partial coverage. Section 706 shows a cost estimate associated with the proposed service, which may include copay amounts, deductible impact, or out-of-pocket costs based on plan parameters. Section 708 identifies whether consent or prior authorization is required. This section may provide a brief description of documentation needs or redirect to a follow-up authorization process. Section 710 lists alternative options, if available, for cases in which the originally intended treatment is not covered. Alternatives may include equivalent medications, generic substitutes, or alternative procedures with lower administrative burden or cost. The interface also includes a set of interactive controls: Submit button 712 allows the physician to proceed with the current treatment plan and confirm the transaction for downstream processing. Override button 714 permits the physician to proceed with a non-covered item, optionally documenting rationale or obtaining patient consent. Cancel button 716 enables the user to exit or discard the current interaction without taking further action.

In this disclosure, the various embodiments are described with reference to the flowchart illustrations and/or block diagrams of methods, apparatus (systems), and computer program products. Those skilled in the art would understand that each block of the flowchart illustrations and/or block diagrams, and combinations of blocks in the flowchart illustrations and/or block diagrams, can be implemented by computer readable program instructions. The computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions or acts specified in the flowchart and/or block diagram block or blocks. The computer readable program instructions can be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can be loaded onto a computer, other programmable data processing apparatus, or other device to cause a series of operational acts to be performed on the computer, other programmable apparatus, or other device to produce a computer implemented process, such that the instructions that execute on the computer, other programmable apparatus, or other device implement the functions or acts specified in the flowchart and/or block diagram block or blocks.

In this disclosure, the block diagrams in the Figures illustrate the architecture, functionality, and operation of possible implementations of systems, methods, and computer program products according to the various embodiments. Each block in the flowchart or block diagrams can represent a module, segment, or portion of instructions, which comprises one or more executable instructions for implementing the specified logical function(s). In some embodiments, the functions noted in the blocks can occur out of the order noted in the Figures. For example, two blocks shown in succession can, in fact, be executed concurrently or substantially concurrently, or the blocks can sometimes be executed in the reverse order, depending upon the functionality involved. In some embodiments, each block of the block diagrams and/or flowchart illustration, and combinations of blocks in the block diagrams and/or flowchart illustration, can be implemented by a special purpose hardware-based system that performs the specified functions or acts or carry out combinations of special purpose hardware and computer instructions.

In this disclosure, the subject matter has been described in the general context of computer-executable instructions of a computer program product running on a computer or computers, and those skilled in the art would recognize that this disclosure can be implemented in combination with other program modules. Generally, program modules include routines, programs, components, data structures, etc. that perform particular tasks and/or implement particular abstract data types. Those skilled in the art would appreciate that the computer-implemented methods disclosed herein can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated embodiments can be practiced in distributed computing environments where tasks are performed by remote processing devices that are linked through a communications network. Some embodiments of this disclosure can be practiced on a stand-alone computer. In a distributed computing environment, program modules can be located in both local and remote memory storage devices.

In this disclosure, the terms "component," "system," "platform," "interface," and the like, can refer to and/or include a computer-related entity or an entity related to an operational machine with one or more specific functionalities. The disclosed entities can be hardware, a combination of hardware and software, software, or software in execution. For example, a component can be a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As another example, a component can be an apparatus that provides specific functionality through electronic components without mechanical parts, wherein the electronic components can include a processor or other means to execute software or firmware that confers at least in part the functionality of the electronic components. In some embodiments, a component can emulate an electronic component via a virtual machine, e.g., within a cloud computing system.

The phrase "application" as is used herein means software other than the operating system, such as Word processors, database managers, Internet browsers and the like. Each application generally has its own user interface, which allows a user to interact with a particular program. The user interface for most operating systems and applications is a graphical user interface (GUI), which uses graphical screen elements, such as windows (which are used to separate the screen into distinct work areas), icons (which are small images that represent computer resources, such as files), pull-down menus (which give a user a list of options), scroll bars (which allow a user to move up and down a window) and buttons (which can be "pushed" with a click of a mouse). A wide variety of applications is known to those in the art.

The phrases "Application Program Interface" and API as are used herein mean a set of commands, functions and/or protocols that computer programmers can use when building software for a specific operating system. The API allows programmers to use predefined functions to interact with an operating system, instead of writing them from scratch. Common computer operating systems, including Windows, Unix, and the Mac OS, usually provide an API for programmers. An API is also used by hardware devices that run software programs. The API generally makes a programmer's job easier, and it also benefits the end user since it generally ensures that all programs using the same API will have a similar user interface.

The phrases "computing device" or "central processing unit" as is used herein means a computer hardware component that executes individual commands of a computer software program. It reads program instructions from a main or secondary memory, and then executes the instructions one at a time until the program ends. During execution, the program may display information to an output device such as a monitor.

The term "execute" as is used herein in connection with a computer, console, server system or the like means to run, use, operate or carry out an instruction, code, software, program and/or the like.

In this disclosure, the descriptions of the various embodiments have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein. Thus, the appended claims should be construed broadly, to include other variants and embodiments, which may be made by those skilled in the art.

It will be appreciated by persons skilled in the art that the present embodiment is not limited to what has been particularly shown and described hereinabove. A variety of modifications and variations are possible considering the above teachings without departing from the following claims.

22

What is claimed is:

1. A computer-implemented method for real-time healthcare transaction processing, comprising:
   receiving, via one or more microphones of a computing device, ambient audio, without directed speech or manual activation, from a healthcare provider-patient conversation;
   transcribing the ambient audio-to-text using a speech recognition engine;
   analyzing transcribed text using a natural language processing engine to identify one or more clinical intents and candidate clinical transaction intents corresponding to healthcare transactions;
   validating a given candidate clinical transaction intent using a context monitoring module that, prior to query generation, requires detection of confirming keywords indicative of decisional language, satisfaction of a temporal proximity threshold within a rolling conversation window, and suppression of duplicate utterances referring to the same clinical action; responsive to the validation;
   suppressing one or more clinical intents unrelated to actionable medical decisions;
   standardizing the identified clinical intent into a structured query format;
   transmitting the structured query over an authenticated, encrypted network session to an external system over a network to request data corresponding to the clinical intent; and
   receiving, via the computing device, a response from the external system, wherein the response comprises at least one of insurance coverage status, patient cost, treatment alternatives, treatment availability, diagnostic alternatives, procedure alternatives, financial assistance program data, optimal referral options, or prior authorization requirement for the clinical intent, and displaying the response in real-time to at least one of the physician or patient during the clinical encounter.

2. The method of claim 1, wherein identifying the clinical intent comprises detecting at least one of a recommendation for medication, imaging, a procedure, or a referral.

3. The method of claim 1, wherein standardizing the identified clinical intent includes mapping recognized keywords to structured formats in accordance with external data schemas.

4. The method of claim 1, wherein the step of receiving ambient audio is performed using a smartphone, tablet, or a web-enabled device positioned in a patient examination room.

5. The method of claim 1, wherein the response is received within less than thirty seconds of a transmission of the structured query.

6. The method of claim 1, further comprising highlighting at least one of alternative treatment, diagnostic, or referral options in a user interface if the external system returns a non-covered status.

7. The method of claim 1, wherein the structured query includes metadata comprising provider information, patient demographics, diagnosis codes, or medication identifiers.

8. The method of claim 1, further comprising storing the clinical intent and external system response in a secure patient record repository.

9. The method of claim 1, further comprising at least one of automatically checking patient eligibility for or automatic enrolling a patient into financial assistance programs based on the response from the external system.

10. A system for automated healthcare transaction processing comprising:

a computing device comprising at least one processor, a memory, and a microphone;

a speech recognition module configured to convert ambient healthcare provider-patient dialogue into a text transcript, without directed speech or manual activation;

a natural language processing module configured to analyze the text transcript and detect one or more candidate clinical transaction intents associated with clinical actions, the module comprising a machine-learning natural-language understanding model;

a query generator module configured to convert the detected transaction intents into structured data queries;

a query generator module configured, responsive to the validation, to standardize the validated clinical transaction intent into a structured data query that conforms to healthcare technology standards comprising CoverageEligibilityRequest, MedicationRequest, and Service-Request and that includes code-mapped fields derived from ICD-10, CPT, and NDC terminology mappings;

a context monitoring module configured to validate a candidate clinical transaction intent by requiring detection of confirming keywords indicative of decisional language, satisfaction of a temporal proximity threshold within a rolling conversation window, and suppression of duplicate utterances referring to a same clinical action;

a user interface module configured to display the transaction results in real-time to the healthcare provider or patient;

wherein the transaction results comprise at least one of a medication coverage, a procedure eligibility, a cost estimate, a prior authorization requirement, or a next-best action for complying with the recommendation comprising automatically scheduling or evaluating calendars for scheduling appointments.

11. The system of claim 10, wherein the natural language processing module utilizes a machine learning model trained on clinical transaction data.

12. The system of claim 10, wherein the communications module is further configured to request and receive prior claims history from the external system.

13. The system of claim 10, wherein the user interface module presents a comparison of covered and non-covered options for a given clinical intent.

14. A non-transitory computer-readable storage medium storing instructions that, when executed by one or more processors, cause a computing system to perform a method comprising:

receiving, without directed speech or manual activation, real-time ambient audio input during a clinical encounter via a microphone;

transcribing the ambient audio into natural language text using a speech recognition engine;

detecting one or more candidate clinical transaction intents from the natural language text using machine learning-based natural language understanding;

validating a given candidate clinical transaction intent using a context monitoring module that, prior to query generation, requires detection of confirming keywords indicative of decisional language, satisfaction of a temporal proximity threshold within a rolling conversation window, and suppression of duplicate utterances referring to the same clinical action; responsive to the validation generating one or more structured queries that conform healthcare technology standards comprising CoverageEligibilityRequest, MedicationRequest, and Service-Request and that include code-mapped fields derived from ICD-10, CPT, and NDC terminology mappings based on the clinical transaction intents;

suppressing queries from the one or more structured queries unrelated to actionable medical decisions;

communicating the structured queries over an authenticated, encrypted network session to an external healthcare administration system;

receiving transaction data in response to the structured queries; and causing a graphical user interface to present the external transaction data to at least one clinical participant during the clinical encounter.

15. The storage medium of claim 14, wherein the machine learning-based natural language understanding is based on transformer-based models fine-tuned on electronic health record data.

16. The storage medium of claim 14, wherein the structured queries conform to a HL7 FHIR protocol standard.

17. The storage medium of claim 14, further comprising logic to determine an urgency of the transaction and prioritize queries accordingly.

18. The storage medium of claim 14, wherein the instructions further cause the system to log rejected transactions for audit and reporting purposes.

19. The storage medium of claim 14, wherein the graphical user interface presents the received transaction data using color-coded indicators based on coverage status.

* * * * *